(12) United States Patent
Washburn et al.

(10) Patent No.: US 11,980,501 B2
(45) Date of Patent: May 14, 2024

(54) METHOD AND SYSTEM FOR PROVIDING ENHANCED ULTRASOUND IMAGES SIMULATING ACQUISITION AT HIGH ACOUSTIC POWER BY PROCESSING ULTRASOUND IMAGES ACQUIRED AT LOW ACOUSTIC POWER

(71) Applicant: GE Precision Healthcare LLC, Milwaukee, WI (US)

(72) Inventors: Michael J. Washburn, Wauwatosa, WI (US); Yelena V. Tsymbalenko, Mequon, WI (US); Heng Zhao, Brookfield, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 773 days.

(21) Appl. No.: 16/783,831

(22) Filed: Feb. 6, 2020

(65) Prior Publication Data
US 2021/0244387 A1    Aug. 12, 2021

(51) Int. Cl.
| | | |
|---|---|---|
| *A61B 8/08* | (2006.01) | |
| *A61B 8/00* | (2006.01) | |
| *G06F 18/214* | (2023.01) | |
| *G06N 20/00* | (2019.01) | |
| *G06V 10/776* | (2022.01) | |
| *G01S 7/52* | (2006.01) | |

(52) U.S. Cl.
CPC .............. *A61B 8/481* (2013.01); *A61B 8/463* (2013.01); *A61B 8/5246* (2013.01); *A61B 8/587* (2013.01); *G06F 18/214* (2023.01); *G06N 20/00* (2019.01); *G06V 10/776* (2022.01); *G01S 7/52052* (2013.01)

(58) Field of Classification Search
None
See application file for complete search history.

(56) References Cited

U.S. PATENT DOCUMENTS

| | | | | |
|---|---|---|---|---|
| 5,833,613 | A | * | 11/1998 | Averkiou ............ G01S 7/52026 600/458 |
| 6,361,510 | B1 | * | 3/2002 | Zanini ...................... A61N 7/00 601/2 |
| 2016/0045186 | A1 | * | 2/2016 | Cong ................... A61B 8/5246 600/440 |
| 2019/0336107 | A1 | * | 11/2019 | Hope Simpson ...... A61B 8/488 |
| 2020/0060652 | A1 | * | 2/2020 | Dahl .................... A61B 8/5269 |

OTHER PUBLICATIONS

Yoon, et al., Efficient B-mode Ultrasound Image Reconstruction from Sub-sampled RF Data using Deep Learning, Senior Member, IEEE, Aug. 7, 2018, pp. 1-12.

* cited by examiner

*Primary Examiner* — Jonathan Cwern
(74) *Attorney, Agent, or Firm* — McAndrews, Held & Malloy, Ltd.; Daniel Bissing; David Bates

(57) ABSTRACT

A system and method for enhancing ultrasound images acquired at a low acoustic power to simulate an acquisition at a high acoustic power is provided. The method may include acquiring, by an ultrasound system, a first ultrasound image at a first acoustic power. The method may include processing, by at least one processor, the first ultrasound image to generate a second ultrasound image simulating a second acoustic power that is greater than the first acoustic power. The method may include presenting the second ultrasound image simulating the second acoustic power at a display system.

17 Claims, 3 Drawing Sheets

METHOD AND SYSTEM FOR PROVIDING ENHANCED ULTRASOUND IMAGES SIMULATING ACQUISITION AT HIGH ACOUSTIC POWER BY PROCESSING ULTRASOUND IMAGES ACQUIRED AT LOW ACOUSTIC POWER

FIELD

Certain embodiments relate to ultrasound imaging. More specifically, certain embodiments relate to a method and system providing an enhanced ultrasound image simulating an acquisition at a high acoustic power by processing an ultrasound image acquired at a low acoustic power.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

Currently, the U.S. Food and Drug Administration (FDA) requires that diagnostic ultrasound imaging systems operate under a certain acoustic output limit for safety reasons. However, ultrasound image quality deteriorates when transmit acoustic power of a same scan target decreases. Contrast-enhanced ultrasound (CEUS) involves the use of microbubble contrast agents and specialized imaging techniques to better visualize blood flow and tissue perfusion information. Accordingly, CEUS transmits much lower acoustic power (e.g., about 10%) than the regular limit to avoid destroying the microbubbles of the contrast agent. In CEUS, a B-mode image with low transmit power is typically displayed side-by-side with the contrast-enhanced image to provide anatomical reference. Due to low transmit power, the reference image often suffers from less penetration, less contrast, lower spatial resolution, and higher background noise, compared to a B-mode image acquired at a typical acoustic power.

Furthermore, the American Institute of Ultrasound in Medicine (AIUM) and the British Medical Ultrasound Society (BMUS) guidelines advocate for lower acoustic power for obstetric ultrasound scans, as well as lower regulatory limits for ophthalmic ultrasound scans. These ultrasound images also have lower quality compared to images acquired with higher acoustic power.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for enhancing ultrasound images acquired at a low acoustic power to simulate an acquisition at a high acoustic power, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
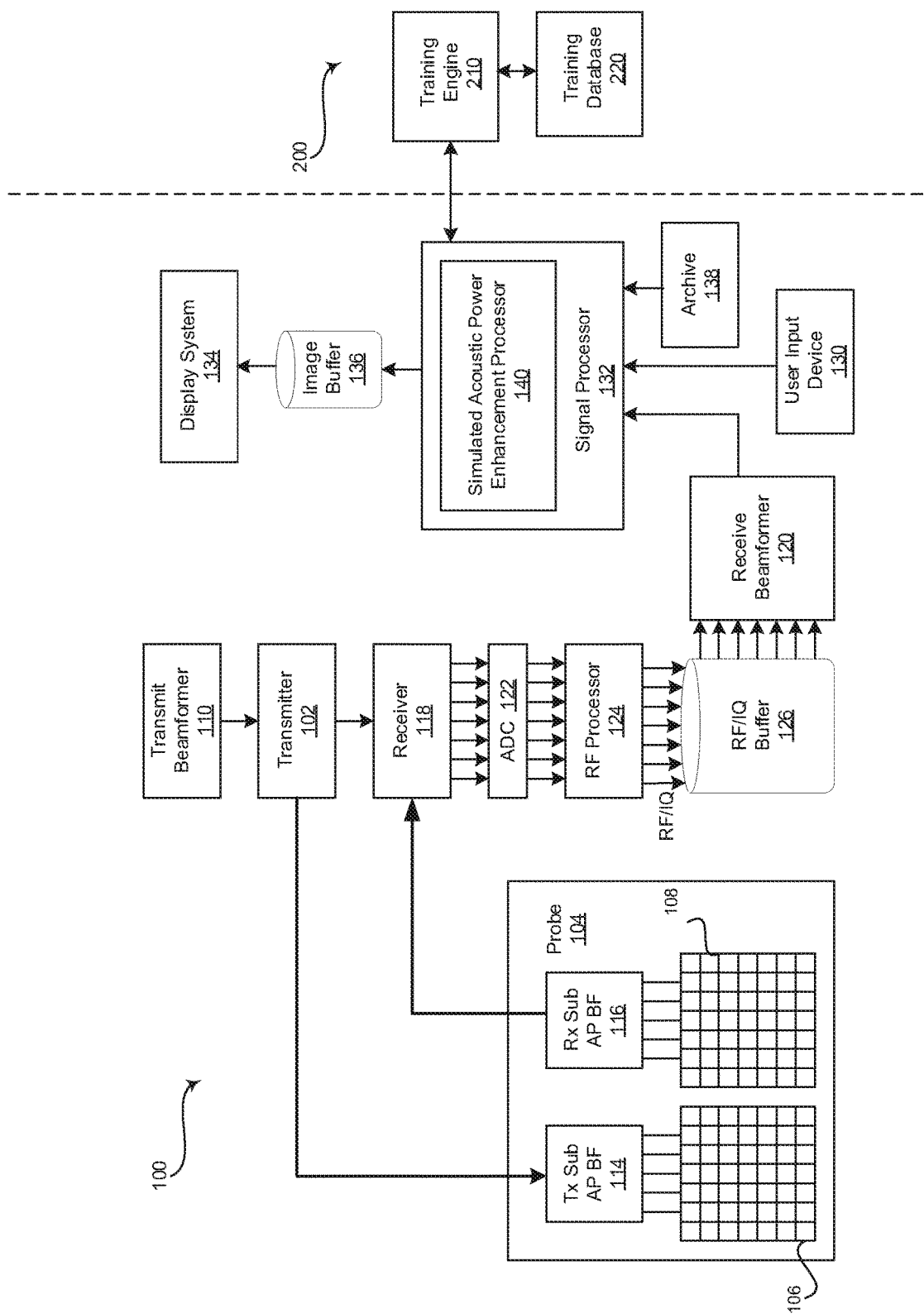
FIG. 1 is a block diagram of an exemplary ultrasound system and training system that is operable to enhance ultrasound images acquired at a low acoustic power to simulate an acquisition at a high acoustic power, in accordance with various embodiments.

Certain embodiments may be found in a method and system for enhancing ultrasound images acquired at a low acoustic power to simulate an acquisition at a high acoustic power. Various embodiments have the technical effect of providing higher quality ultrasound images by enhancing images acquired with low or limited acoustic output without destroying contrast agent or exceeding safety limits. Aspects of the present disclosure have the technical effect of enhancing image quality for ultrasound applications and/or modes that require lower or limited transmit acoustic power.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, Contrast Enhanced Ultrasound (CEUS), and/or sub-modes of B-mode and/or CF such as Harmonic Imaging, Shear Wave Elasticity Imaging (SWEI), Strain Elastography, TVI, PDI, B-flow, MVI, UGAP, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 and training system 200 that is operable to enhance ultrasound images acquired at a low acoustic power to simulate an acquisition at a high acoustic power, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and, an archive 138.

The transmitter 102 may comprise suitable logic, circuitry, interfaces and/or code that may be operable to drive an ultrasound probe 104. The ultrasound probe 104 may comprise a two-dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or a plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, graphic processing units, microprocessors, microcontrollers, and/or the like. The signal processor 132 may be an integrated component, or may be distributed across various locations, for example. In an exemplary embodiment, the signal processor 132 may comprise a simulated acoustic power enhancement processor 140 and may be capable of receiving input information from a user input device 130 and/or archive 138, generating an output displayable by a display system 134, and manipulating the output in response to input information from a user input device 130, among other things. The signal processor 132 and simulated acoustic power enhancement processor 140 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a simulated acoustic power enhancement processor 140 that comprises suitable logic, circuitry, interfaces and/or code that may be operable to process low acoustic power ultrasound images to generate ultrasound images simulating a high acoustic power. For example, the simulated acoustic power enhancement processor 140 may receive ultrasound images acquired at low acoustic power, such as contrast-enhanced ultrasound (CEUS) reference images, obstetric ultrasound images, ophthalmic ultrasound images, images with acoustic power levels within U.S. Food and Drug Administration (FDA) limits, and/or any suitable ultrasound image acquired at a low acoustic power. The simulated acoustic power enhancement processor 140 may be configured to generate ultrasound images enhancing the contrast resolution, spatial resolution, reduce noise, and the like such that the generated ultrasound images appear to have been acquired at a higher acoustic power. In a representative embodiment, the simulated acoustic power enhancement processor 140 may include artificial intelligence models/deep neural networks (e.g., a convolutional neural network) and/or may utilize any suitable form of artificial intelligence image processing techniques or machine learning processing functionality configured to process the ultrasound images acquired at a low acoustic power to generate ultrasound images having a simulated higher acoustic power.

The simulated acoustic power enhancement processor 140 may comprise suitable logic, circuitry, interfaces and/or code that may be operable to enhance ultrasound images acquired at a low acoustic power to simulate an acquisition at a high acoustic power. In various embodiments, the simulated acoustic power enhancement processor 140 may deploy deep neural network(s) (e.g., artificial intelligence model(s)) that may be made up of, for example, an input layer, an output layer, and one or more hidden layers in between the input and output layers. Each of the layers may be made up of a plurality of processing nodes that may be referred to as neurons. For example, the simulated acoustic power enhancement processor 140 may inference an artificial intelligence model comprising an input layer having a neuron for each pixel or a group of pixels from a scan plane of an anatomical structure. The output layer may have neurons corresponding to enhanced pixels of a generated ultrasound image simulating acquisition at a higher acoustic power. As an example, the output layer may generate an enhanced ultrasound image having reduced noise and increased contrast resolution and spatial resolution to simulate an acoustic power that is greater than the acoustic power at which the input ultrasound image was acquired. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the simulated acoustic power enhancement processor 140 inferencing the deep neural network (e.g., convolutional neural network) may enhance low acoustic power ultrasound image data with a high degree of probability.

In an exemplary embodiment, the simulated acoustic power enhancement processor 140 may comprise suitable logic, circuitry, interfaces and/or code that may be operable to process a low acoustic power ultrasound image by registering and matching the low acoustic power ultrasound image with a previously acquired ultrasound image of a same patient anatomy acquired at a higher acoustic power. The simulated acoustic power enhancement processor 140 may be configured to blend and/or combine the registered and matched low and high acoustic power images to generate the enhanced ultrasound image simulating the acoustic power that is higher than the low acoustic power ultrasound image.

The simulated acoustic power enhancement processor 140 may comprise suitable logic, circuitry, interfaces and/or code that may be operable to register and match low acoustic power ultrasound images with high acoustic power ultrasound images. In various embodiments, the simulated acoustic power enhancement processor 140 may deploy a deep neural network that may be made up of, for example, an input layer, an output layer, and one or more hidden layers in between the input and output layers. Each of the layers may be made up of a plurality of processing nodes that may be referred to as neurons. For example, the simulated acoustic power enhancement processor 140 may inference an artificial intelligence model comprising an input layer having a neuron for each pixel or a group of pixels from a scan plane of an anatomical structure. The output layer may have a neuron corresponding to locations of landmarks and/or identified anatomical structures. As an example, the output layer may include neurons for nerve locations, vessel locations, bone locations, organ locations, or any suitable anatomical structure location. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the simulated acoustic power enhancement processor 140 deploying the deep neural network (e.g., convolutional neural network) may register and match anatomical structures in low and high acoustic power ultrasound images with a high degree of probability.

Still referring to FIG. 1, the display system 134 may be any device capable of communicating visual information to a user. For example, a display system 134 may include a liquid crystal display, a light emitting diode display, and/or any suitable display or displays. The display system 134 can be operable to present ultrasound images and/or any suitable information. For example, the display system 134 may be operable to present enhanced ultrasound images simulating acquisition at a high acoustic power, and or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound images acquired at a low acoustic power, ultrasound images acquired at a high acoustic power, enhanced ultrasound images simulating a high acoustic power, artificial intelligence models deployable to generate enhanced ultrasound images, artificial intelligence models for registering and matching high and low acoustic power ultrasound images, and instructions for blending and/or combining registered and matched high and low acoustic power ultrasound images, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 160 may comprise suitable logic, circuitry, interfaces and/or code that may be operable to train the neurons of the deep neural network(s) (e.g., artificial intelligence model(s)) inferenced (i.e., deployed) by the simulated acoustic power enhancement processor 140. For example, the artificial intelligence model inferenced by the simulated acoustic power enhancement processor 140 may be trained to automatically process low acoustic power ultrasound images to generate ultrasound images simulating acquisition at a higher acoustic power by enhancing contrast resolution, spatial resolution, and reducing noise in the received ultrasound images acquired at the low acoustic power. For example, the training engine 210 may train the deep neural networks deployed by the simulated acoustic power enhancement processor 140 using database(s) 220 of classified pairs of ultrasound images of various structures. The pairs of ultrasound images may include a first ultrasound image acquired at a low acoustic power and a second ultrasound image of a same anatomical structure acquired at a high acoustic power. In various embodiments, the anatomical structure of the high acoustic power ultrasound image may be simulated using tissue mimicking phantoms, such that FDA limits may be exceeded during the ultrasound scan. As an example, the artificial intelligence models inferenced by the simulated acoustic power enhancement processor 140 may be trained by the training engine 210 with pairs of ultrasound images having different acoustic power acquisition levels to train the models deployed by the simulated acoustic power enhancement processor 140 with respect to the characteristics of the image data acquired at different acoustic power levels, such as the appearance of structure edges, the appearance of structure shapes based on the edges, the appearance and/or presence of noise, and the like.

As another example, deep neural network(s) inferenced by the simulated acoustic power enhancement processor 140 may be trained to automatically register and match an ultrasound image acquired at low acoustic power with an ultrasound image acquired at high acoustic power. For example, the training engine 210 may train the deep neural network(s) inferenced by the simulated acoustic power enhancement processor 140 using databases(s) 220 of classified ultrasound images of various structures. The ultrasound images may include images of anatomical structures acquired at different acoustic power levels. As an example, the deep neural network(s) inferenced by the simulated acoustic power enhancement processor 140 may be trained by the training engine 210 with ultrasound images of various anatomical structures at different acoustic power acquisition levels to train the deep neural network(s) deployed by the simulated acoustic power enhancement processor 140 with respect to the characteristics of the anatomical structure(s) depicted in the acquired image data, such as the appearance of structure edges, the appearance of structure shapes based on the edges, the positions of the shapes relative to landmarks in the ultrasound image data, and the like. In an exemplary embodiment, the structure positions may include nerve locations, vessel locations, bone locations, organ locations, or any suitable anatomical structure location. The structural information may include information regarding the edges, shapes, and positions of organs, nerves, vessels, tissue, and/or the like.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

Figure 2:
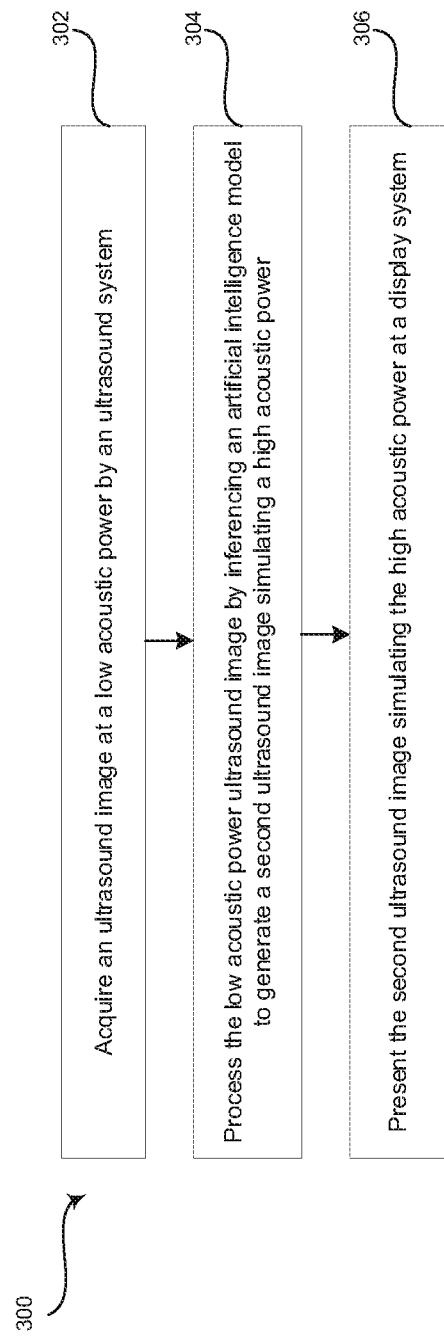
FIG. 2 is a flow chart illustrating exemplary steps that may be utilized for enhancing ultrasound images acquired at a low acoustic power to simulate an acquisition at a high acoustic power, in accordance with various embodiments.

FIG. 2 is a flow chart 300 illustrating exemplary steps 302-306 that may be utilized for enhancing ultrasound images acquired at a low acoustic power to simulate an acquisition at a high acoustic power, in accordance with various embodiments. Referring to FIG. 2, there is shown a flow chart 300 comprising exemplary steps 302 through 306. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 302, an ultrasound system 100 acquires an ultrasound image at a low acoustic power. For example, the ultrasound system 100 may acquire an ultrasound image with an ultrasound probe 104 positioned at a scan position over region of interest. The acoustic power applied to acquire the image may be a low level, such as within FDA limits and/or according to ALUM and/or BMUS guidelines. The acquired ultrasound image may be a CEUS image, an obstetric ultrasound image, an ophthalmic ultrasound image, or any suitable image.

At step 304, a signal processor 132 of the ultrasound system 100 may process the low acoustic power ultrasound image by inferencing an artificial intelligence model to generate a second ultrasound image simulating a high acoustic power. For example, a simulated acoustic power enhancement processor 140 of the signal processor 132 may be configured to enhance the contrast resolution, spatial resolution, reduce noise, and the like of the ultrasound image acquired at step 302 to generate an ultrasound image having the appearance of an image acquired at an acoustic power higher than the acoustic power that the acquired ultrasound image was obtained. The simulated acoustic power enhancement processor 140 may deploy artificial intelligence models, artificial intelligence image processing algorithms, and/or may utilize any suitable form of artificial intelligence image processing techniques or machine learning processing functionality configured to process low acoustic power ultrasound images to generate enhanced ultrasound images simulating acquisition at a higher acoustic power. For example, the ultrasound image acquired at step 302 may be acquired at an acoustic power below the FDA limit and the generated ultrasound image at step 304 may simulate an acoustic power above the FDA limit. As another example, the ultrasound image acquired at step 302 may be acquired with a microbubble contrast agent and the ultrasound image generated at step 304 may be a simulated acoustic power that would burst the microbubbles of the contrast agent.

At step 306, the second ultrasound image simulating the high acoustic power may be presented at a display system 134. For example, the simulated acoustic power enhancement processor 140 of the signal processor 132 may present the enhanced ultrasound image simulating the acquisition at the higher acoustic power level generated at step 304 at the display system 134.

Figure 3:
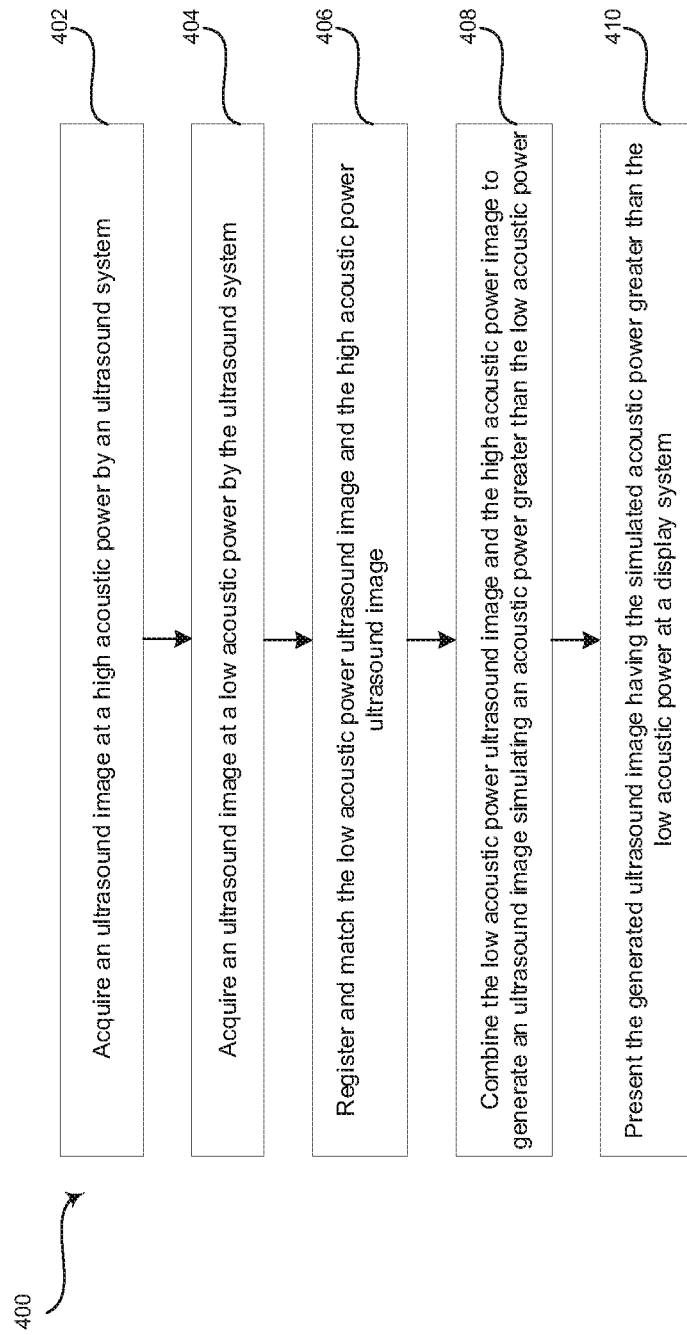
FIG. 3 is a flow chart illustrating exemplary steps that may be utilized for enhancing ultrasound images acquired at a low acoustic power to simulate an acquisition at a high acoustic power, in accordance with various embodiments.

FIG. 3 is a flow chart 400 illustrating exemplary steps 402-410 that may be utilized for enhancing ultrasound images acquired at a low acoustic power to simulate an acquisition at a high acoustic power, in accordance with various embodiments. Referring to FIG. 3, there is shown a flow chart 400 comprising exemplary steps 402 through 410. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, an ultrasound system 100 acquires an ultrasound image at a high acoustic power. For example, the ultrasound system 100 may acquire an ultrasound image with an ultrasound probe 104 positioned at a scan position over region of interest. The acoustic power applied to acquire the image may be at a high level, such as at or near the highest level allowed by FDA limits and/or prior to introducing a microbubble contrast agent in a CEUS examination.

At step 404, an ultrasound system 100 acquires an ultrasound image at a low acoustic power. For example, the ultrasound system 100 may acquire an ultrasound image with an ultrasound probe 104 positioned at a scan position over region of interest. The acoustic power applied to acquire the image may be lower than the acoustic power applied at step 402. For example, the acquired ultrasound image may be a CEUS image (i.e., after the microbubble contrast agent has been introduced), or any suitable image. In various embodiments, the image acquired at step 404 is of a same patient and same anatomical structure as the image acquired at step 402.

At step 406, a signal processor 132 of the ultrasound system 100 may register and match the low acoustic power ultrasound image and the high acoustic power ultrasound image. For example, a simulated acoustic power enhancement processor 140 of the signal processor 132 may be configured to register and match the low acoustic power ultrasound image acquired at step 404 with the high acoustic power ultrasound image acquired at step 402. The simulated acoustic power enhancement processor 140 may include artificial intelligence image processing algorithms, one or more deep neural networks (e.g., a convolutional neural network) and/or may utilize any suitable form of artificial intelligence image analysis techniques or machine learning processing functionality configured to analyze, register, and match the low acoustic power and high acoustic power ultrasound images.

At step 408, the signal processor 132 of the ultrasound system 100 may combine the low acoustic power ultrasound image and the high acoustic power ultrasound image to generate an ultrasound image simulating an acoustic power greater than the low acoustic power. For example, the simulated acoustic power enhancement processor 140 of the signal processor 132 may be configured to combine and/or blend the low and high acoustic power ultrasound images registered and matched at step 406 to generate an enhanced ultrasound image simulating an acoustic power that is greater than the low acoustic power ultrasound image.

At step 410, the generated ultrasound image simulating an acoustic power that is greater than the low acoustic power may be presented at a display system 134. For example, the simulated acoustic power enhancement processor 140 of the signal processor 132 may present the enhanced ultrasound image simulating the acquisition at the higher acoustic power level generated at step 408 at the display system 134.

Aspects of the present disclosure provide a method 300, 400 and system 100 for enhancing ultrasound images acquired at a low acoustic power to simulate an acquisition at a high acoustic power. In accordance with various embodiments, the method 300, 400 may comprise acquiring 302, 404, by an ultrasound system 100, a first ultrasound image at a first acoustic power. The method 300, 400 may comprise processing 304, 406, 408, by at least one processor 132, 140, the first ultrasound image to generate a second ultrasound image simulating a second acoustic power that is greater than the first acoustic power. The method 300, 400 may comprise presenting 306, 410, at a display system 134, the second ultrasound image simulating the second acoustic power.

In an exemplary embodiment, an artificial intelligence model may be inferenced by the at least one processor 132, 140 to process the first ultrasound image to generate the second ultrasound image simulating the second acoustic power. In a representative embodiment, the first ultrasound image may be acquired with a microbubble contrast agent and the simulated second acoustic power may be a power that would burst the microbubble contrast agent. In certain embodiments, the first acoustic power may be within Food and Drug Administration (FDA) limits. The second acoustic power may exceed the FDA limits. In various embodiments, the method 300 may comprise training the artificial intelligence model inferenced by the at least one processor 132, 140 based on pairs of training images. Each of the pairs of training images may comprise a first training image acquired at an acoustic power and a second training image acquired at a higher acoustic power than the acoustic power of the first training image. In an exemplary embodiment, the second training image of each of the pairs of training images may be acquired from tissue mimicking phantoms. In a representative embodiment, the method 400 may comprise acquiring 402, by the ultrasound system 100, a third ultrasound image at a third acoustic power greater than the first acoustic power at a same region of interest prior to acquisition of the first ultrasound image. The method 400 may comprise registering and matching 406, by the at least one processor 132, 140, the first ultrasound image to the third ultrasound image. The processing the first ultrasound image may comprise combining 408, by the at least one processor 132, 140, the first ultrasound image with the second ultrasound image to generate the second ultrasound image simulating the second acoustic power that is greater than the first acoustic power.

Various embodiments provide a system 100 for enhancing ultrasound images acquired at a low acoustic power to simulate an acquisition at a high acoustic power. The system 100 may comprise an ultrasound system 100, at least one processor 132, 140, and a display system 134. The ultrasound system 100 may be configured to acquire a first ultrasound image at a first acoustic power. The at least one processor 132, 140 may be configured to process the first ultrasound image to generate a second ultrasound image simulating a second acoustic power that is greater than the first acoustic power. The display system 134 may be configured to present the second ultrasound image simulating the second acoustic power.

In a representative embodiment, the at least one processor 132, 140 may be configured to inference an artificial intelligence model to process the first ultrasound image to generate the second ultrasound image simulating the second acoustic power. In an exemplary embodiment, the ultrasound system 100 may be configured to acquire the first ultrasound image with a microbubble contrast agent and the simulated second acoustic power is a power that would burst the microbubble contrast agent. In certain embodiments, the first acoustic power may be within Food and Drug Administration (FDA) limits. The second acoustic power may exceed the FDA limits. In various embodiments, the artificial intelligence model inferenced by the at least one processor 132, 140 may be trained based on pairs of training images. Each of the pairs of training images may comprise a first training image acquired at an acoustic power and a second training image acquired at a higher acoustic power than the acoustic power of the first training image. In a representative embodiment, the second training image of each of the pairs of training images may be acquired from tissue mimicking phantoms. In an exemplary embodiment, the ultrasound system 100 may be configured to acquire a third ultrasound image at a third acoustic power greater than the first acoustic power at a same region of interest prior to acquiring the first ultrasound image. The at least one processor 132, 140 may be configured to register and match the first ultrasound image to the third ultrasound image. The at least one processor 132, 140 may be configured to process the first ultrasound image by combining the first ultrasound image with the second ultrasound image to generate the second ultrasound image simulating the second acoustic power that is greater than the first acoustic power.

Certain embodiments provide a non-transitory computer readable medium having stored thereon, a computer program having at least one code section. The at least one code section is executable by a machine for causing the machine to perform steps 300, 400. The steps 300, 400 may comprise receiving 302, 404 a first ultrasound image acquired at a first acoustic power. The steps 300, 400 may comprise processing 304, 406, 408 the first ultrasound image to generate a second ultrasound image simulating a second acoustic power that is greater than the first acoustic power. The steps 300, 400 may comprise presenting 306, 410 the second ultrasound image simulating the second acoustic power at a display system.

In various embodiments, the processing 304 the first ultrasound image to generate the second ultrasound image simulating the second acoustic power is performed by inferencing an artificial intelligence model. In certain embodiments, the first ultrasound image may be acquired with a microbubble contrast agent and the simulated second acoustic power may be a power that would burst the microbubble contrast agent. In a representative embodiment, the first acoustic power may be within Food and Drug Administration (FDA) limits. The second acoustic power may exceed the FDA limits. In an exemplary embodiment, the steps 300, 400 may comprise training the artificial intelligence model based on pairs of training images. Each of the pairs of training images may comprise a first training image acquired at an acoustic power and a second training image acquired at a higher acoustic power than the acoustic power of the first training image. In various embodiments, the steps 400 may comprise receiving 402 a third ultrasound image acquired at a third acoustic power greater than the first acoustic power at a same region of interest prior to receiving the first ultrasound image. The steps 400 may comprise registering and matching 406 the first ultrasound image to the third ultrasound image. The processing 406, 408 the first ultrasound image may comprise combining 408 the first ultrasound image with the second ultrasound image to generate the second ultrasound image simulating the second acoustic power that is greater than the first acoustic power.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for enhancing ultrasound images acquired at a low acoustic power to simulate an acquisition at a high acoustic power.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
acquiring, by an ultrasound system, a first ultrasound image at a first acoustic power, the first ultrasound image having a plurality of a first contrast resolution, a first spatial resolution, and/or a first amount of noise, wherein the first ultrasound image comprises a plurality of pixels;
processing, by at least one processor, the plurality of pixels of the first ultrasound image to generate a second ultrasound image simulating a second acoustic power that is greater than the first acoustic power, the second ultrasound image having a plurality of a second contrast resolution greater than the first contrast resolution, a second spatial resolution greater than the first spatial resolution, and/or a second amount of noise less than the first amount of noise; and
presenting, at a display system, the second ultrasound image simulating the second acoustic power.

2. The method of claim 1, wherein an artificial intelligence model is inferenced by the at least one processor to process the first ultrasound image to generate the second ultrasound image simulating the second acoustic power.

3. The method of claim 2, wherein the first ultrasound image is acquired with a microbubble contrast agent and the simulated second acoustic power is a power that would burst the microbubble contrast agent.

4. The method of claim 2, comprising training the artificial intelligence model inferenced by the at least one processor based on pairs of training images, each of the pairs of training images comprising a first training image acquired at an acoustic power and a second training image acquired at a higher acoustic power than the acoustic power of the first training image.

5. The method of claim 4, wherein the second training image of each of the pairs of training images is acquired from tissue mimicking phantoms.

6. The method of claim 1, comprising:
acquiring, by the ultrasound system, a third ultrasound image at a third acoustic power greater than the first acoustic power at a same region of interest prior to acquisition of the first ultrasound image, the third ultrasound image having a plurality of a third contrast resolution greater than the first contrast resolution, a third spatial resolution greater than the first spatial resolution, and/or a third amount of noise less than the first amount of noise, and
registering and matching, by the at least one processor, the first ultrasound image to the third ultrasound image,
wherein the processing the first ultrasound image comprises combining, by the at least one processor, the first ultrasound image with the third ultrasound image to generate the second ultrasound image simulating the second acoustic power that is greater than the first acoustic power.

7. A system comprising:
an ultrasound system configured to acquire a first ultrasound image at a first acoustic power, the first ultrasound image having a plurality of a first contrast resolution, a first spatial resolution, and/or a first amount of noise, wherein the first ultrasound image comprises a plurality of pixels;
at least one processor configured to process the plurality of pixels of the first ultrasound image to generate a second ultrasound image simulating a second acoustic power that is greater than the first acoustic power, the second ultrasound image having a plurality of a second contrast resolution greater than the first contrast resolution, a second spatial resolution greater than the first spatial resolution, and/or a second amount of noise less than the first amount of noise; and a display system configured to present the second ultrasound image simulating the second acoustic power.

8. The system of claim 7, wherein the at least one processor is configured to inference an artificial intelligence model to process the first ultrasound image to generate the second ultrasound image simulating the second acoustic power.

9. The system of claim 8, wherein the ultrasound system is configured to acquire the first ultrasound image with a microbubble contrast agent and the simulated second acoustic power is a power that would burst the microbubble contrast agent.

10. The system of claim 8, wherein the artificial intelligence model inferenced by the at least one processor is trained based on pairs of training images, each of the pairs of training images comprising a first training image acquired at an acoustic power and a second training image acquired at a higher acoustic power than the acoustic power of the first training image.

11. The system of claim 10, wherein the second training image of each of the pairs of training images is acquired from tissue mimicking phantoms.

12. The system of claim 7, wherein:
the ultrasound system is configured to acquire a third ultrasound image at a third acoustic power greater than the first acoustic power prior to acquiring the first ultrasound image at a same region of interest, the third ultrasound image having a plurality of a third contrast resolution greater than the first contrast resolution, a third spatial resolution greater than the first spatial resolution, and/or a third amount of noise less than the first amount of noise,
the at least one processor is configured to register and match the first ultrasound image to the third ultrasound image, and
the at least one processor is configured to process the first ultrasound image by combining the first ultrasound image with the third ultrasound image to generate the second ultrasound image simulating the second acoustic power that is greater than the first acoustic power.

13. A non-transitory computer readable medium having stored thereon, a computer program having at least one code section, the at least one code section being executable by a machine for causing the machine to perform steps comprising:

receiving a first ultrasound image acquired at a first acoustic power, the first ultrasound image having a plurality of a first contrast resolution, a first spatial resolution, and/or a first amount of noise, wherein the first ultrasound image comprises a plurality of pixels;

processing the plurality of pixels of the first ultrasound image to generate a second ultrasound image simulating a second acoustic power that is greater than the first acoustic power the second ultrasound image having a plurality of a second contrast resolution greater than the first contrast resolution, a second spatial resolution greater than the first spatial resolution, and/or a second amount of noise less than the first amount of noise; and presenting the second ultrasound image simulating the second acoustic power at a display system.

14. The non-transitory computer readable medium of claim 13, wherein the processing the first ultrasound image to generate the second ultrasound image simulating the second acoustic power is performed by inferencing an artificial intelligence model.

15. The non-transitory computer readable medium of claim 14, wherein the first ultrasound image is acquired with a microbubble contrast agent and the simulated second acoustic power is a power that would burst the microbubble contrast agent.

16. The non-transitory computer readable medium of claim 14, comprising training the artificial intelligence model based on pairs of training images, each of the pairs of training images comprising a first training image acquired at an acoustic power and a second training image acquired at a higher acoustic power than the acoustic power of the first training image.

17. The non-transitory computer readable medium of claim 13, comprising:
receiving a third ultrasound image acquired at a third acoustic power greater than the first acoustic power at a same region of interest prior to receiving the first ultrasound image, the third ultrasound image having a plurality of a third contrast resolution greater than the first contrast resolution, a third spatial resolution greater than the first spatial resolution, and/or a third amount of noise less than the first amount of noise, and
registering and matching the first ultrasound image to the third ultrasound image,
wherein the processing the first ultrasound image comprises combining the first ultrasound image with the third ultrasound image to generate the second ultrasound image simulating the second acoustic power that is greater than the first acoustic power.

* * * * *